US010488349B2

(12) United States Patent  
Sibbach (10) Patent No.: US 10,488,349 B2  
(45) Date of Patent: Nov. 26, 2019

(54) AUTOMATED BORESCOPE INSERTION SYSTEM

(71) Applicant: General Electric Company, Schenectady, NY (US)

(72) Inventor: Arthur William Sibbach, Boxford, MA (US)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 15/812,004

(22) Filed: Nov. 14, 2017

(65) Prior Publication Data

US 2019/0145905 A1  May 16, 2019

(51) Int. Cl.
| | |
|---|---|
| G01N 21/954 | (2006.01) |
| G02B 23/24 | (2006.01) |
| H04N 7/18 | (2006.01) |

(52) U.S. Cl.  
CPC ....... G01N 21/954 (2013.01); G02B 23/2484 (2013.01); H04N 7/183 (2013.01)

(58) Field of Classification Search  
None  
See application file for complete search history.

(56) References Cited

U.S. PATENT DOCUMENTS

| | | | |
|---|---|---|---|
| 3,694,094 A | 9/1972 | Mitchell | |
| 4,562,392 A * | 12/1985 | Davis | G01B 21/10 |
| | | | 318/39 |
| 4,699,463 A | 10/1987 | D'Amelio et al. | |
| 5,253,638 A | 10/1993 | Tamburrino et al. | |
| 5,345,339 A | 9/1994 | Knieriem et al. | |
| 5,549,542 A | 8/1996 | Kovalcheck | |
| 5,850,469 A | 12/1998 | Martin et al. | |
| 6,124,974 A | 9/2000 | Burger | |
| 6,134,003 A | 10/2000 | Tearney et al. | |
| 6,483,535 B1 | 11/2002 | Tamburrino et al. | |
| 6,560,013 B1 | 5/2003 | Ramsbottom | |
| 6,753,876 B2 | 6/2004 | Brooksby et al. | |
| 6,793,399 B1 | 9/2004 | Nguyen | |
| 7,064,811 B2 | 6/2006 | Twerdochlib | |
| 7,171,279 B2 | 1/2007 | Buckingham et al. | |
| 7,901,348 B2 | 3/2011 | Soper et al. | |

(Continued)

OTHER PUBLICATIONS

U.S. Appl. No. 15/671,502, filed Aug. 8, 2017.  
U.S. Appl. No. 15/278,541, filed Sep. 28, 2016.

*Primary Examiner* — Reza Aghevli  
(74) *Attorney, Agent, or Firm* — Dority & Manning, P.A.

(57) ABSTRACT

A system for inserting and orienting a probe into a machine includes a probe, a cable insertion unit, and a computer communicatively coupled to both the probe and cable insertion unit. The probe includes at least one sensor and a cable. Further, the at least one sensor produces at least one signal. The cable insertion unit is configured to orient and feed the probe. The computer includes an installed digital model of the machine. Further, the computer is configured to receive the at least one signal from the probe and produce a location model. The location model includes at least one of a two dimensional or three dimensional model representing the probe's real-time location relative to the machine. As such, the cable insertion unit orients and feeds the probe into the machine under the guidance of the computer.

20 Claims, 8 Drawing Sheets

(56) References Cited

U.S. PATENT DOCUMENTS

| | | |
|---|---|---|
| 7,914,446 B2 | 3/2011 | Keller |
| 8,139,103 B2 | 3/2012 | McGrew |
| 8,311,738 B2 | 11/2012 | Politick et al. |
| 8,451,459 B2 * | 5/2013 | Hynous ............... G01B 11/026 356/614 |
| 8,485,038 B2 | 7/2013 | Sengupta et al. |
| 8,602,722 B2 | 12/2013 | George et al. |
| 8,950,004 B2 | 2/2015 | Messinger et al. |
| 9,002,112 B2 | 4/2015 | France |
| 9,026,247 B2 | 5/2015 | White et al. |
| 9,036,892 B2 | 5/2015 | Domke et al. |
| 9,149,929 B2 | 10/2015 | Motzer et al. |
| 9,218,470 B2 | 12/2015 | Domke et al. |
| 9,458,735 B1 | 10/2016 | Diwinsky et al. |
| 9,476,823 B2 | 10/2016 | Ward et al. |
| 9,551,620 B2 | 1/2017 | Singh et al. |
| 9,641,125 B2 | 5/2017 | Johnston |
| 9,710,573 B2 | 7/2017 | Messinger et al. |
| 9,715,100 B2 | 7/2017 | Konomura et al. |
| 2005/0199832 A1 | 9/2005 | Twerdochlib |
| 2006/0025668 A1 | 2/2006 | Peterson et al. |
| 2006/0247511 A1 | 11/2006 | Anderson |
| 2008/0186018 A1 | 8/2008 | Anderson |
| 2008/0238413 A1 | 10/2008 | Anderson |
| 2009/0079426 A1 | 3/2009 | Anderson |
| 2009/0096443 A1 | 4/2009 | Anderson |
| 2009/0118620 A1 | 5/2009 | Tgavalekos et al. |
| 2010/0113917 A1 | 5/2010 | Anderson |
| 2011/0059016 A1 * | 3/2011 | Ramanujam ......... A61B 5/0059 424/9.1 |
| 2012/0105619 A1 | 5/2012 | PallikkaraGopalan et al. |
| 2012/0203067 A1 | 8/2012 | Higgins et al. |
| 2013/0113915 A1 | 5/2013 | Scheid et al. |
| 2013/0192353 A1 * | 8/2013 | Hatcher ................ F01D 21/003 73/112.01 |
| 2013/0194412 A1 * | 8/2013 | Hatcher ................ F01D 21/003 348/82 |
| 2013/0194413 A1 * | 8/2013 | Hatcher ............. G02B 23/2476 348/82 |
| 2013/0335530 A1 * | 12/2013 | Hatcher, Jr. ........ G02B 23/2484 348/46 |
| 2013/0335549 A1 * | 12/2013 | Hatcher, Jr. ........ G02B 23/2484 348/82 |
| 2014/0098091 A1 | 4/2014 | Hori |
| 2014/0161338 A1 * | 6/2014 | Machado ............. A61B 5/0042 382/131 |
| 2014/0207419 A1 | 7/2014 | Messinger et al. |
| 2015/0022655 A1 | 1/2015 | Ruhge |
| 2015/0172567 A1 | 6/2015 | Ekeroth |
| 2015/0300920 A1 * | 10/2015 | DeAscanis ............ G01M 15/14 356/614 |
| 2015/0319410 A1 | 11/2015 | Gu et al. |
| 2015/0338353 A1 * | 11/2015 | Bancalari ............. F01D 21/003 348/82 |
| 2015/0341600 A1 * | 11/2015 | Hatcher, Jr. ........... H04N 7/183 348/82 |
| 2016/0011080 A1 * | 1/2016 | Moore .................. F01D 25/285 73/112.01 |
| 2016/0025653 A1 | 1/2016 | Jalilian et al. |
| 2016/0088204 A1 | 3/2016 | Liang et al. |
| 2016/0178533 A1 | 6/2016 | Gladnick |
| 2016/0330351 A1 * | 11/2016 | DeAscanis ............ H04N 5/2251 |
| 2017/0122123 A1 | 5/2017 | Kell et al. |
| 2017/0148309 A1 | 5/2017 | Messinger et al. |
| 2017/0167285 A1 | 6/2017 | Diwinsky et al. |
| 2017/0167289 A1 | 6/2017 | Diwinsky et al. |
| 2017/0219814 A1 * | 8/2017 | Letter ................ G02B 23/2476 |
| 2017/0219815 A1 * | 8/2017 | Letter ................ H04N 5/23238 |
| 2017/0223273 A1 | 8/2017 | Bendall et al. |

* cited by examiner

AUTOMATED BORESCOPE INSERTION SYSTEM

FIELD

The present subject matter relates generally to a probe for inspection of a machine, and more particularly to a system and method for automated probe insertion into a machine.

BACKGROUND

Optical scopes are used as an inspection tool to view inside an apparatus such as a turbomachine or engine. Optical scopes, such as borescopes, include a removable optical adapter tip at an end of the optical scope. The optical adapter is generally suited for various purposes, such as providing a discrete direction of view. The optical scope, including the optical adapter, is ingressed into the apparatus for viewing and assessing internal components.

In order to allow for periodic inspection of internal parts of the engine (e.g., blades, vanes, shrouds, disks, frames, etc.), borescope ports are typically provided in the engine casings and/or frames. Such ports allow optical borescope instruments to be inserted into the core engine to enable a visual inspection of the engine to be performed without requiring disassembly of the engine components. However, once an instrument has been inserted into a borescope port, minimal information is typically available to an inspector regarding the actual position of the instrument within the engine, leading to errors in measurements and reducing the efficiency of performing the visual inspection.

Adding to these inefficiencies, many borescope examinations are controlled manually by the inspector. More specifically, the inspector inserts and manipulates the borescope to achieve the desired view of the apparatus. This manual control of the borescope can lead to irregular and/or inconsistent video during the insertion of the borescope probe, thereby reducing the quality of the borescope inspection. Further, trial and error of the human operator can lead to longer inspection times, increased maintenance costs, loss or damage of the borescope within the apparatus, and/or damage to the apparatus.

As such, there is a need for a system and method of borescope examination that may mitigate borescope insertion trial and error, improve inspection quality, improve inspection time and cost, and mitigate losses and damages to the borescope or surrounding apparatus.

BRIEF DESCRIPTION

Aspects and advantages of the invention will be set forth in part in the following description, or may be obvious from the description, or may be learned through practice of the invention.

In one aspect, the present disclosure is directed to a system for inserting and orienting a probe into a machine. The system includes a probe, a cable insertion unit, and a computer communicatively coupled to both the probe and cable insertion unit. The probe includes at least one sensor and a cable. As such, the at least one sensor produces at least one signal. The cable insertion unit is configured to orient and feed the probe. The computer includes an installed digital model of the machine. Further, the computer is configured to receive the at least one signal from the probe and produce a location model. The location model includes at least one of a two dimensional or three dimensional model representing the probe's real-time location relative to the machine. As such, the cable insertion unit orients and feeds the probe into the machine under the guidance of the computer.

In one embodiment, at least one sensor may include an optical sensor. In a further embodiment, the system may include a first display configured to show the video signal from the optical sensor. In another embodiment, at least one sensor may include a proximity sensor. In an additional embodiment, the computer may further include a probe computing unit and a processor with memory. The probe computing unit is configured to receive the signal from the probe and create a modified signal. The processor with memory is configured to store the digital model of the machine and receive the modified signal from the probe computing unit. The processor further communicatively coupled to and in control of the cable insertion unit.

In further embodiments, the cable insertion unit may include a 3D gimbal with servo motor control on each of three axes. In another embodiment the system may include a second display configured to show the location model representing the probe's real-time location relative to the machine. In one embodiment, the probe may further include at least one other sensor. As such, the signal from the sensor(s) is transmitted to the computer and used by the computer to determine the real-time location of the probe. In an additional embodiment, the computer may be communicatively coupled to at least one control system of the machine. More specifically, the control system is used to manipulate the machine before, after, or while orienting and feeding the probe into the machine.

In another aspect, the present disclosure is directed to a method of automated probe insertion into a machine. The method includes attaching a cable insertion unit to the machine at an access port. Another step includes feeding a probe into the cable insertion unit. The probe includes at least one sensor and cable. Yet another step includes transferring the signal from the probe to a computer installed with a digital model of the machine. The computer is configured to produce a location model representing the probe's real-time location relative to the machine. Further, the computer is communicatively coupled to and in control of the probe insertion unit. The method also includes inserting the probe into the machine using the cable insertion unit under the guidance of the computer. More specifically, the computer automatically sends signals to the cable insertion unit to feed and orient the probe.

In another embodiment, the method may include receiving a new signal at the computer from changing data at the probe. In a further embodiment, the method may include changing the real-time location of the probe in the location model based on the new signal. In yet another embodiment, changing the real-time location of the probe may include recognizing a known location in the signal and altering the real-time location of the probe to that location in the location model. In a further embodiment, the method may include altering the insertion speed and orientation automatically via the computer to lead the probe to a desired target location.

In a different embodiment, the method may include setting an initial location of the probe in the location model to the access port of the machine. In an additional embodiment, the method may include sending a signal from the computer to the probe to generally adjust an orientation of a probe tip. In yet another embodiment, the guidance of the computer may include an algorithm that learns the most efficient method of moving the probe to a target location, by storing and processing data from multiple insertions to the same or similar target locations.

In another aspect, the present disclosure is directed to a method for determining the real-time location of a probe in a machine. The method includes placing the probe near an internal object that has a known location. Further, the probe includes a sensor and cable. Another step includes transferring the signal from the probe to a computer installed with a digital model of the machine. The method also includes producing a location model of the real-time location of the probe in relation to the machine.

In a different embodiment, the probe may include at least one other sensor. As such, the signal from the other sensor is transferred to the computer to determine the real-time location of the probe in the location model. In another embodiment, the method may include displaying the location model on a display.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

A system is generally provided for inserting and orienting a probe into a machine, along with methods of automated probe insertion into a machine and methods of determining the real-time location of a probe in a machine. For example, in one embodiment, the system includes a probe, a cable insertion unit, and a computer communicatively coupled to both the probe and cable insertion unit. The probe includes at least one sensor and a cable. The at least one sensor produces at least one signal. The cable insertion unit is configured to orient and feed the probe. The computer includes an installed digital model of the machine. Further, the computer is configured to receive the at least one signal from the probe and produce a location model. The location model includes at least one of a two dimensional or three dimensional model representing the probe's real-time location relative to the machine. As such, the cable insertion unit orients and feeds the probe into the machine under the guidance of the computer.

In certain embodiments, automatic insertion of a probe via computer eliminates the need for human trial and error in orienting and inserting the probe. The computer may also contain algorithms to learn and store the most efficient methods for accessing specific locations within the target machine, by storing and processing data from multiple insertions to the same or similar target locations. Furthermore, this system may be adapted for use with a wide variety of commercially available borescopes and for inspecting any machine. The use of computer controlled insertion allows for a smooth video signal that the operator can observe during insertion. More specifically, irregular and/or inconsistent video during human controlled insertion may be avoided, thereby increasing the quality of the probe inspection. Further, the disclosed system can lead to reduced maintenance costs, avoidance of loss or damage to the probe within the machine, and/or prevention of damage to the machine.

It should be appreciated that, although the present subject matter will generally be described herein with reference to inserting and determining the location of an optical probe within a gas turbine engine, the disclosed system and method may be generally used to insert any probe within a gas turbine engine and determine the location of the probe.

For instance, the system and method may be used to insert and determine the location of a repair probe to be inserted within a gas turbine engine via one of its access ports to allow for a given repair procedure to be performed within the engine.

It should also be appreciated that the disclosed system and method may generally be used to insert and locate probes within any suitable type of turbine engine, including aircraft-based turbine engines, land-based turbine engines, and/or steam turbine engines, regardless of the current assembly state of the engine (e.g., fully or partially assembled). Additionally, with reference to aircraft engines, it should be appreciated that the present subject matter may be used on wing or off wing.

Furthermore, it should be appreciated that, although the present subject matter will generally be described herein with reference to inserting and determining the location of an optical probe within a gas turbine engine, the disclosed system and method may be generally used to insert and determine the location of any probe within any type of machine. More specifically, the system and method may generally be used on any machine with internal structure that is difficult to access and/or inspect.

Figure 1:
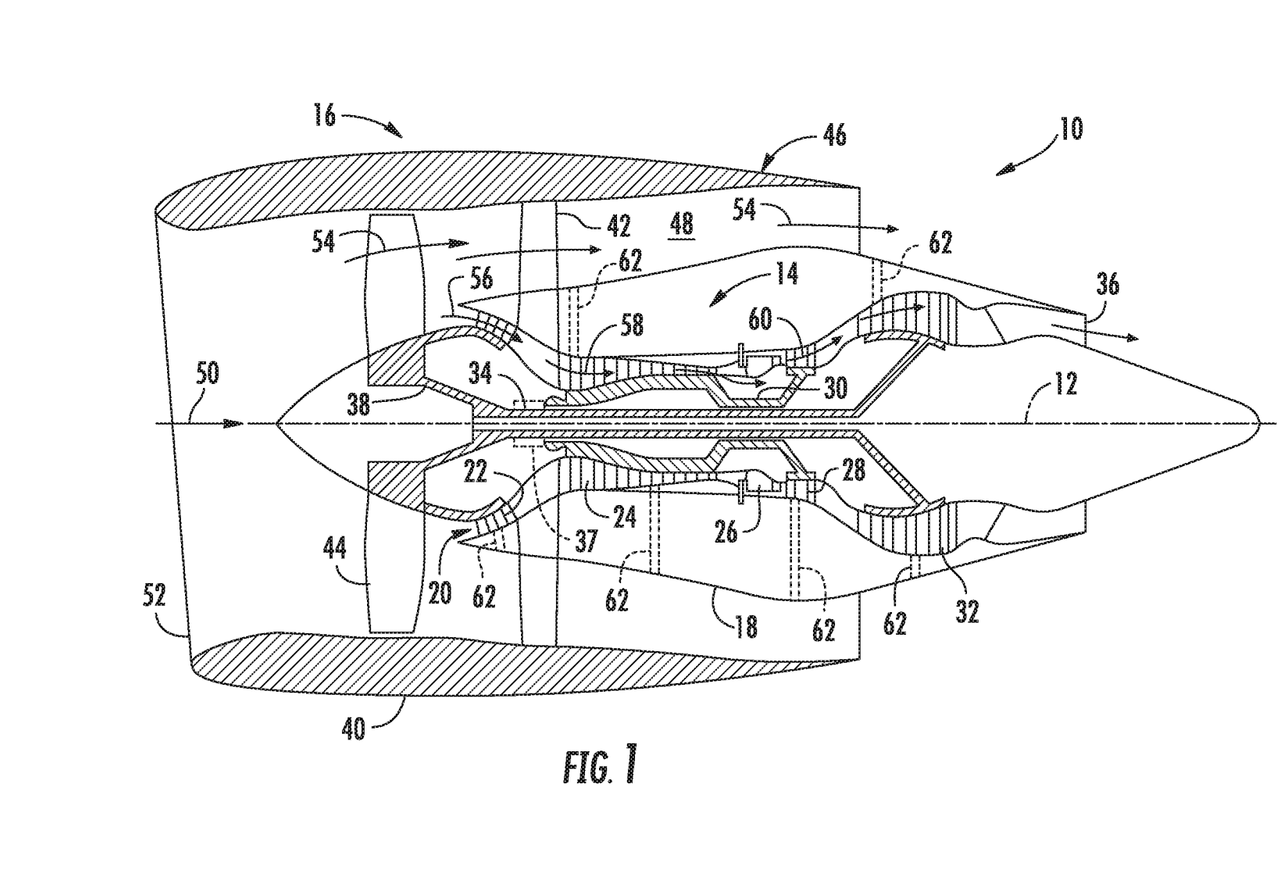
FIG. 1 illustrates a cross-sectional view of one embodiment of a gas turbine engine that may be utilized in accordance with aspects of the present subject matter.

Referring now to the drawings, FIG. 1 illustrates a cross-sectional view of one embodiment of a gas turbine engine 10 that may be utilized within an aircraft in accordance with aspects of the present subject matter, with the engine 10 being shown having a longitudinal or axial centerline axis 12 extending therethrough for reference purposes. In general, the engine 10 may include a core gas turbine engine (indicated generally by reference character 14) and a fan section 16 positioned upstream thereof. The core engine 14 may generally include a substantially tubular outer casing 18 that defines an annular inlet 20. In addition, the outer casing 18 may further enclose and support a booster compressor 22 for increasing the pressure of the air that enters the core engine 14 to a first pressure level. A high pressure, multi-stage, axial-flow compressor 24 may then receive the pressurized air from the booster compressor 22 and further increase the pressure of such air. The pressurized air exiting the high-pressure compressor 24 may then flow to a combustor 26 within which fuel is injected into the flow of pressurized air, with the resulting mixture being combusted within the combustor 26. The high energy combustion products are directed from the combustor 26 along the hot gas path of the engine 10 to a first (high pressure) turbine 28 for driving the high pressure compressor 24 via a first (high pressure) drive shaft 30, and then to a second (low pressure) turbine 32 for driving the booster compressor 22 and fan section 16 via a second (low pressure) drive shaft 34 that is generally coaxial with first drive shaft 30. After driving each of turbines 28 and 32, the combustion products may be expelled from the core engine 14 via an exhaust nozzle 36 to provide propulsive jet thrust.

Additionally, as shown in FIG. 1, the fan section 16 of the engine 10 may generally include a rotatable, axial-flow fan rotor assembly 38 that is configured to be surrounded by an annular fan casing 40. It should be appreciated by those of ordinary skill in the art that the fan casing 40 may be configured to be supported relative to the core engine 14 by a plurality of substantially radially-extending, circumferentially-spaced outlet guide vanes 42. As such, the fan casing 40 may enclose the fan rotor assembly 38 and its corresponding fan rotor blades 44. Moreover, a downstream section 46 of the fan casing 40 may extend over an outer portion of the core engine 14 so as to define a secondary, or by-pass, airflow conduit 48 that provides additional propulsive jet thrust.

It should be appreciated that, in several embodiments, the second (low pressure) drive shaft 34 may be directly coupled to the fan rotor assembly 38 to provide a direct-drive configuration. Alternatively, the second drive shaft 34 may be coupled to the fan rotor assembly 38 via a speed reduction device 37 (e.g., a reduction gear or gearbox) to provide an indirect-drive or geared drive configuration. Such a speed reduction device(s) may also be provided between any other suitable shafts and/or spools within the engine 10 as desired or required.

During operation of the engine 10, it should be appreciated that an initial air flow (indicated by arrow 50) may enter the engine 10 through an associated inlet 52 of the fan casing 40. The air flow 50 then passes through the fan blades 44 and splits into a first compressed air flow (indicated by arrow 54) that moves through conduit 48 and a second compressed air flow (indicated by arrow 56) which enters the booster compressor 22. The pressure of the second compressed air flow 56 is then increased and enters the high pressure compressor 24 (as indicated by arrow 58). After mixing with fuel and being combusted within the combustor 26, the combustion products 60 exit the combustor 26 and flow through the first turbine 28. Thereafter, the combustion products 60 flow through the second turbine 32 and exit the exhaust nozzle 36 to provide thrust for the engine 10.

The gas turbine engine 10 may also include a plurality of access ports defined through its casings and/or frames for providing access to the interior of the core engine 14. For instance, as shown in FIG. 1, the engine 10 may include a plurality of access ports 62 (only six of which are shown) defined through the outer casing 18 for providing internal access to one or both of the compressors 22, 24 and/or for providing internal access to one or both of the turbines 28, 32. In several embodiments, the access ports 62 may be spaced apart axially along the core engine 14. For instance, the access ports 62 may be spaced apart axially along each compressor 22, 24 and/or each turbine 28, 32 such that at least one access port 62 is located at each compressor stage and/or each turbine stage for providing access to the internal components located at such stage(s). In addition, the access ports 62 may also be spaced apart circumferentially around the core engine 14. For instance, a plurality of access ports 62 may be spaced apart circumferentially around each compressor stage and/or turbine stage.

It should be appreciated that, although the access ports 62 are generally described herein with reference to providing internal access to one or both of the compressors 22, 24 and/or for providing internal access to one or both of the turbines 28, 32, the gas turbine engine 10 may include access ports 62 providing access to any suitable internal location of the engine 10, such as by including access ports 62 that provide access within the combustor 26 and/or any other suitable component of the engine 10.

Figure 2:
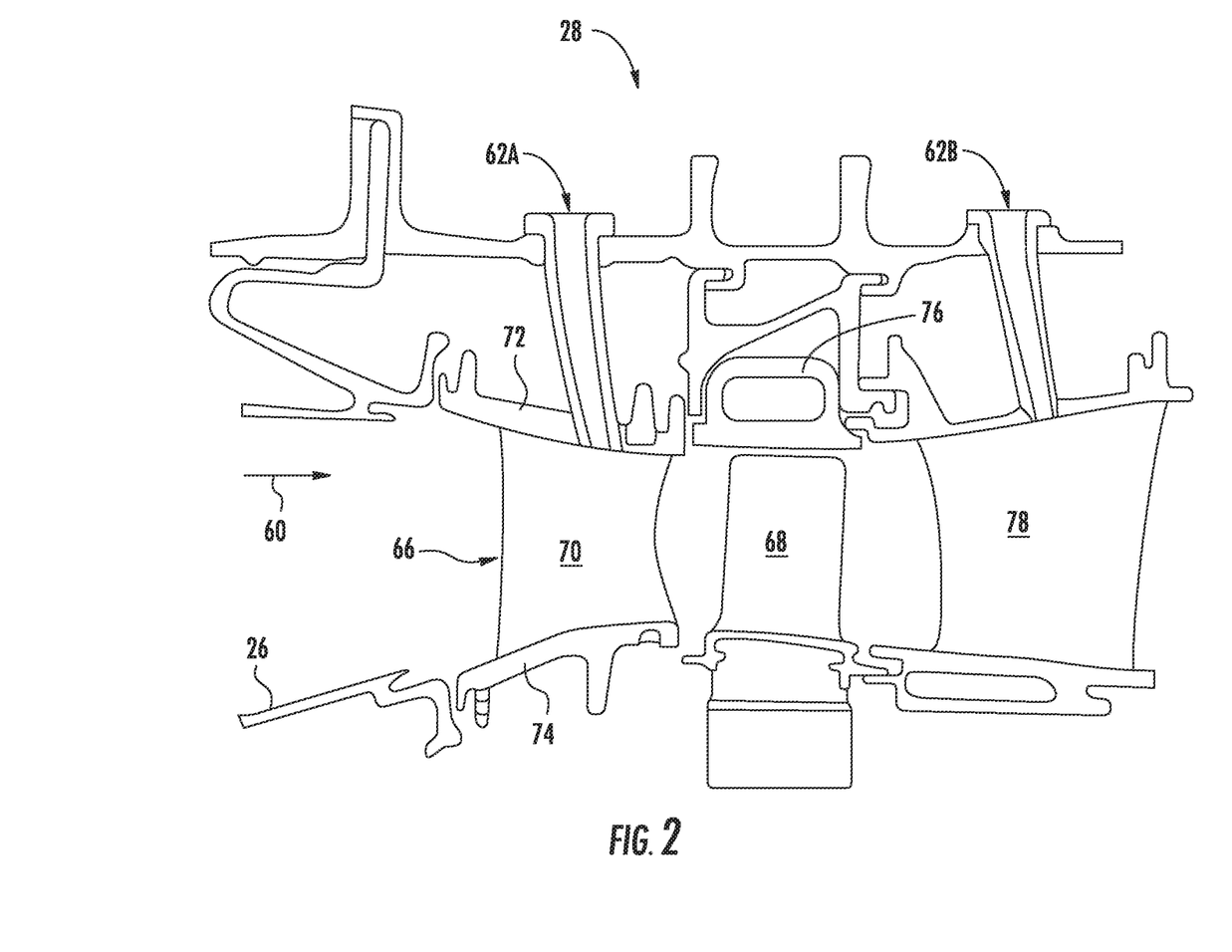
FIG. 2 illustrates a partial, cross-sectional view of a portion of the gas turbine engine shown in FIG. 1, particularly illustrating access ports defined in the engine for providing internal access.

Referring now to FIG. 2, a partial, cross-sectional view of the first (or high pressure) turbine 28 described above with reference to FIG. 1 is illustrated in accordance with embodiments of the present subject matter. As shown, the first turbine 28 may include a first stage turbine nozzle 66 and an annular array of rotating turbine blades 68 (one of which is shown) located immediately downstream of the nozzle 66. The nozzle 66 may generally be defined by an annular flow channel that includes a plurality of radially-extending, circularly-spaced nozzle vanes 70 (one of which is shown). The vanes 70 may be supported between a number of arcuate outer bands 72 and arcuate inner bands 74. Additionally, the circumferentially spaced turbine blades 68 may generally be configured to extend radially outwardly from a rotor disk (not shown) that rotates about the centerline axis 12 (FIG. 1) of the engine 10. Moreover, a turbine shroud 76 may be positioned immediately adjacent to the radially outer tips of the turbine blades 68 so as to define the outer radial flowpath boundary for the combustion products 60 flowing through the turbine 28 along the hot gas path of the engine 10.

As indicated above, the turbine 28 may generally include any number of turbine stages, with each stage including an annular array of nozzle vanes and follow-up turbine blades 68. For example, as shown in FIG. 2, an annular array of nozzle vanes 78 of a second stage of the turbine 28 may be located immediately downstream of the turbine blades 68 of the first stage of the turbine 28.

Moreover, as shown in FIG. 2, a plurality of access ports 62 may be defined through the turbine casing and/or frame, with each access port 62 being configured to provide access to the interior of the turbine 28 at a different axial location. Specifically, as indicated above, the access ports 62 may, in several embodiments, be spaced apart axially such that each access port 62 is aligned with or otherwise provides interior access to a different stage of the turbine 28. For instance, as shown in FIG. 2, a first access port 62A may be defined through the turbine casing/frame to provide access to the first stage of the turbine 28 while a second access port 62B may be defined through the turbine casing/frame to provide access to the second stage of the turbine 28.

It should be appreciated that similar access ports 62 may also be provided for any other stages of the turbine 28 and/or for any turbine stages of the second (or low pressure) turbine 32. It should also be appreciated that, in addition to the axially spaced access ports 62 shown in FIG. 2, access ports 62 may be also provided at differing circumferentially spaced locations. For instance, in one embodiment, a plurality of circumferentially spaced access ports may be defined through the turbine casing/frame at each turbine stage to provide interior access to the turbine 28 at multiple circumferential locations around the turbine stage.

Figure 3:
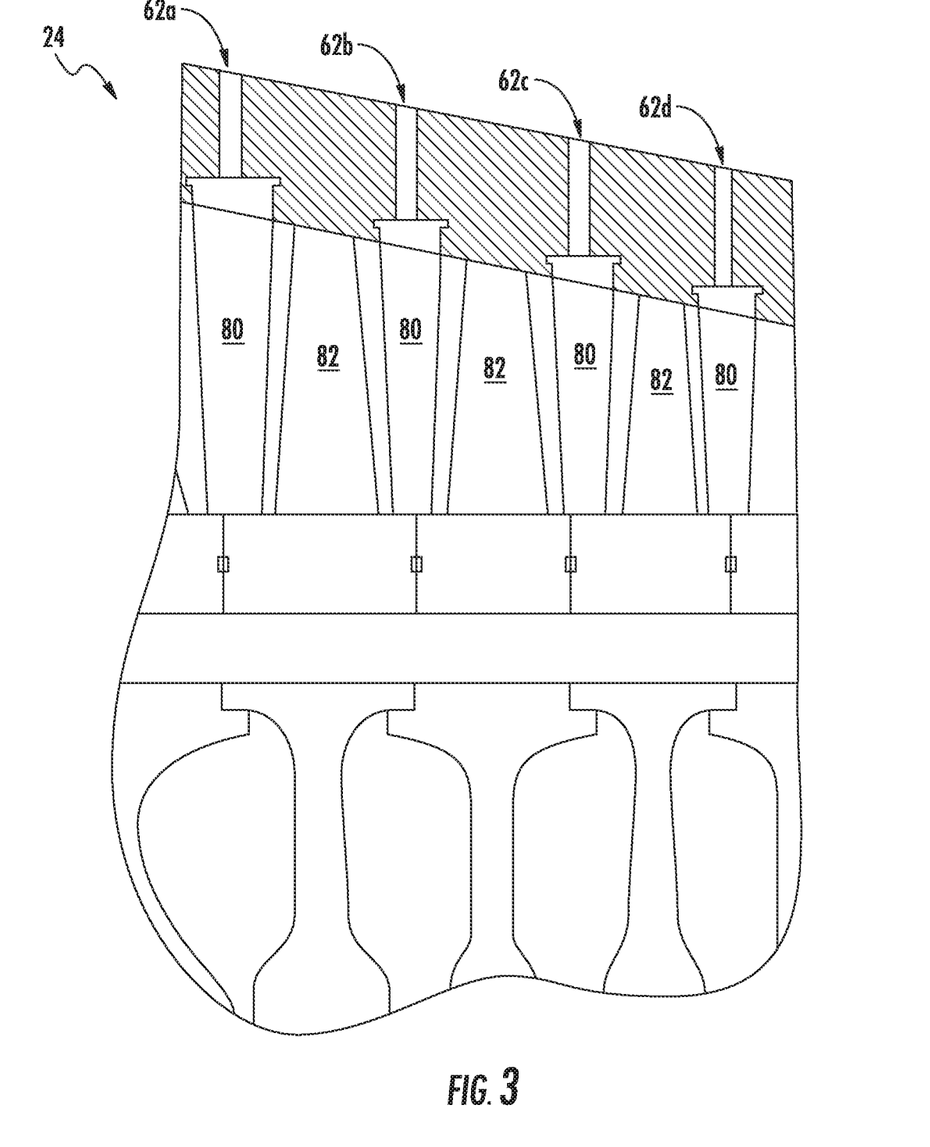
FIG. 3 illustrates a partial, cross-sectional view of one embodiment of a compressor suitable for use within the gas turbine engine shown in FIG. 1, particularly illustrating access ports defined in the engine for providing internal access to the compressor.

Referring now to FIG. 3, a partial, cross-sectional view of the high pressure compressor 24 described above with reference to FIG. 1 is illustrated in accordance with embodiments of the present subject matter. As shown, the compressor 24 may include a plurality of compressor stages, with each stage including both an annular array of fixed compressor vanes 80 (only one of which is shown for each stage) and an annular array of rotatable compressor blades 82 (only one of which is shown for each stage). Each row of compressor vanes 80 is generally configured to direct air flowing through the compressor 24 to the row of compressor blades 82 immediately downstream thereof.

Moreover, the compressor 24 may include a plurality of access ports 62 defined through the compressor casing/frame, with each access port 62 being configured to provide access to the interior of the compressor 24 at a different axial location. Specifically, in several embodiments, the access ports 62 may be spaced apart axially such that each access port 62 is aligned with or otherwise provides interior access to a different stage of the compressor 24. For instance, as shown in FIG. 3, first, second, third and fourth access ports 62a, 62b, 62c, 62d are illustrated that provide access to four successive stages, respectively, of the compressor 24.

It should be appreciated that similar access ports 62 may also be provided for any of the other stages of the compressor 24 and/or for any of the stages of the low pressure compressor 22. It should also be appreciated that, in addition to the axially spaced access ports 62 shown in FIG. 3, access ports 62 may be also provided at differing circumferentially spaced locations. For instance, in one embodiment, a plurality of circumferentially spaced access ports 62 may be defined through the compressor casing/frame at each compressor stage to provide interior access to the compressor 24 at multiple circumferential locations around the compressor stage.

Figure 4:
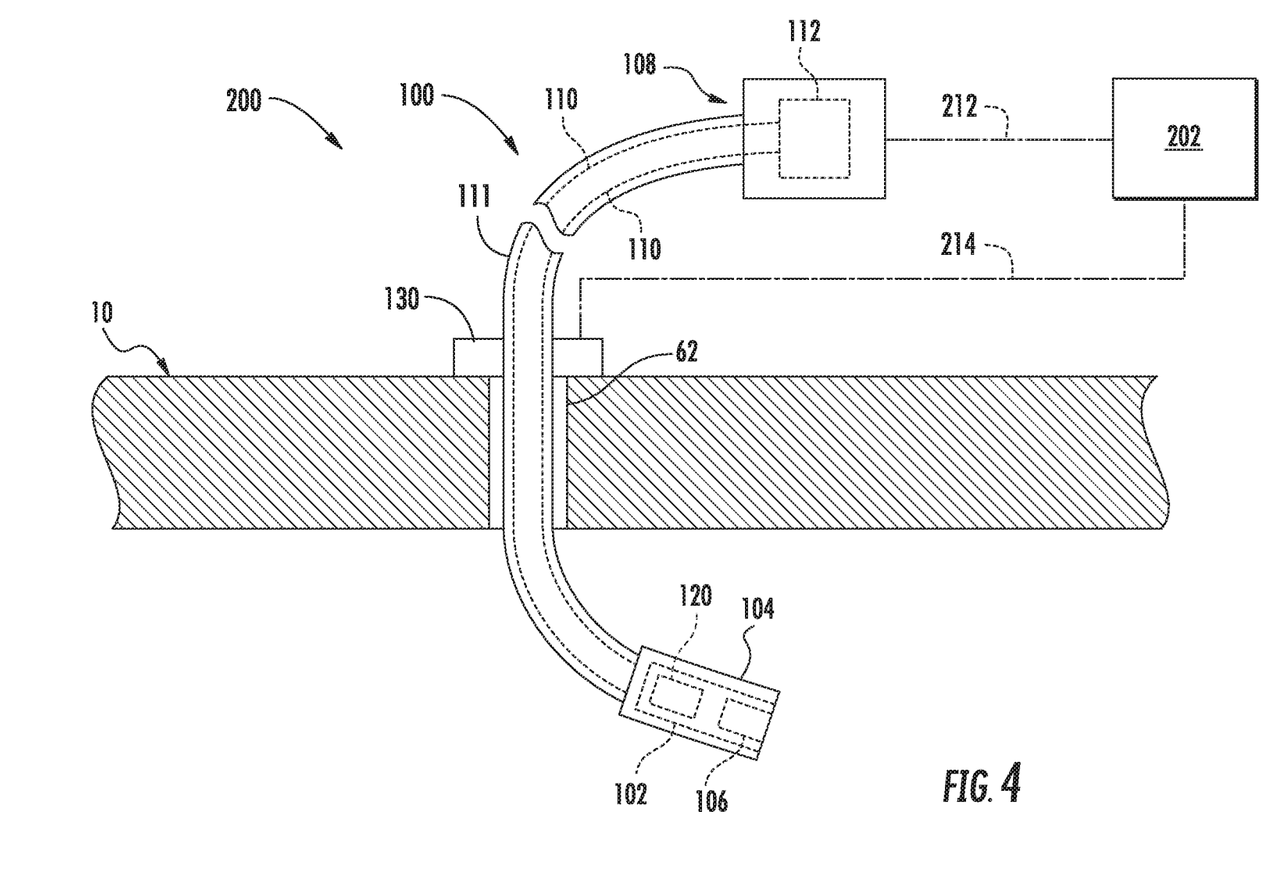
FIG. 4 illustrates a simplified view of one embodiment of a probe that may be used in accordance with aspects of the present subject matter to visually inspect a gas turbine engine and a system for the automatic insertion and orientation of the probe.
Figure 5:
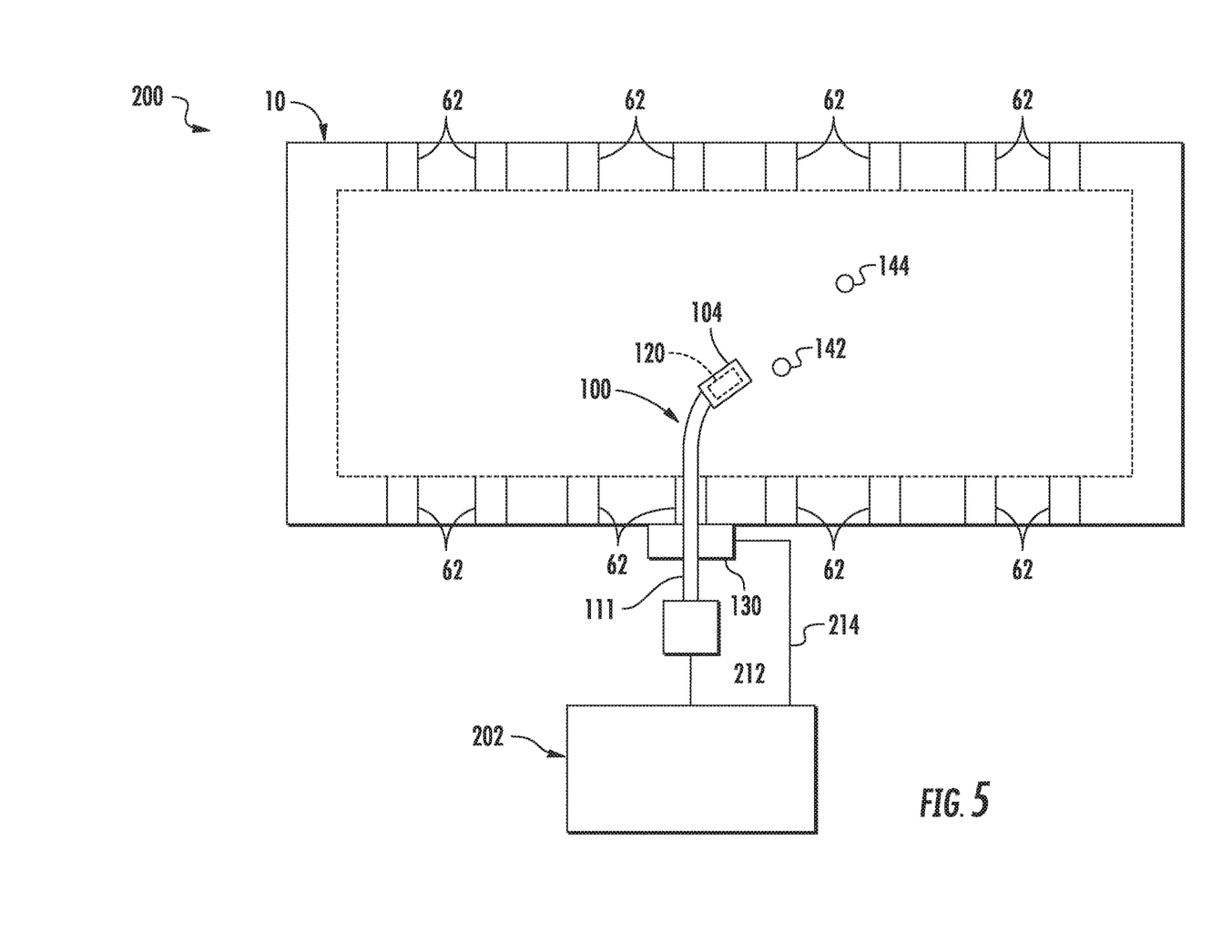
FIG. 5 illustrates a simplified, schematic view of one embodiment of a system for automatically inserting and orienting a probe within a gas turbine engine in accordance with aspects of the present subject matter.

Referring now to FIGS. 4 and 5, simplified views of one embodiment of a system 200 for inserting and orienting a probe 100 into a gas turbine engine 10 is illustrated in accordance with aspects of the present subject matter. As shown, the probe 100 has been inserted through an access port 62 of the engine 10, such as any of the access ports 62 described above with reference to FIGS. 1-3.

More specifically, as shown, the system 200 includes the probe 100, a cable insertion unit 130, and a computer 202 communicatively coupled to both the probe 100 and the cable insertion unit 130. The probe 100 includes at least one sensor 120 and cable 111. As such, the sensor 120 produces a signal that is communicated through the cable 111 and to the computer 202 via the communicative cable 212. Further, the computer 202 is communicatively coupled to the cable insertion unit 130 via communicative cable 214. The computer 202 is configured to orient and feed the probe 110 while it is inserted and oriented into the turbine engine 10. More specifically, the computer 202 sends signals via the communicative cable 214 to the cable insertion unit 130 to change the orientation of the probe 100 and the rate the probe 100 is fed into the turbine engine 10.

In general, the probe 100 may correspond to any suitable probe configured to be inserted within the gas turbine engine 10 via an access port 62. Specifically, as shown in the illustrated embodiment, the probe 100 corresponds to an optical probe 100. In such an embodiment, the optical probe 100 may correspond to any suitable optical device that may be inserted through an access port 62 of the gas turbine engine 10 to allow images of the interior of the engine 10 to be captured or otherwise obtained. For instance, in several embodiments, the optical probe 100 may correspond to a borescope, videoscope, fiberscope, or any other similar optical device known in the art that allows for the interior of a gas turbine engine 10 to be viewed through an access port 62.

In such embodiments, a sensor housing 102 may include one or more optical elements, such as one or more optical lenses, optical fibers, image capture devices (e.g., video cameras, still-image cameras, CCD devices, CMOS devices), cables, and/or the like, for obtaining views or images of the interior of the engine 10 at a tip 104 of the probe 100 and for transmitting or relaying such images from the probe tip 104 along the length of the probe 100 to the exterior of the engine 10. As such, the sensor housing 102 may include a sensor 120 such as an optical sensor. For instance, as shown in FIG. 4, the interior views or images obtained by the probe 100 may be transmitted from the probe tip 104 to the computer 202 connected or otherwise coupled to the probe 100 via communicative cable 212. Additionally, as shown in FIG. 4, in one embodiment, a light source 106, such as an LED, may be provided at or adjacent to the probe tip 104 to provide lighting within the interior of the engine 10.

In one embodiment, the probe may further include at least one other sensor 120. As such, the signal from the sensor(s) 120 is transmitted to the computer 202 and may be used by the computer 202 to determine the real-time location of the probe 100 and/or for inspection purposes. More specifically, in one embodiment, at least one sensor 120 may include a proximity sensor. Proximity sensors may include generally sensors that at least emit or retrieve electromagnetic signals and process changes in said electromagnetic signals. For example, proximity sensors may include, but are not limited to, capacitive, infrared, inductive, magnetic, sonic or ultrasonic proximity sensors, LIDAR, RADAR, or laser rangefinders.

The probe 100 may also include an articulation assembly 108 that allows the orientation of the probe tip 104 to be adjusted within the interior of the gas turbine engine 10. For example, the articulation assembly 108 may allow for the probe tip 104 to be rotated or pivoted about a single axis or multiples axes to adjust the orientation of the tip 104 relative to the remainder of the probe 100. It should be appreciated that the articulation assembly 108 may generally have any suitable configuration and/or may include any suitable components that allow for adjustment of the orientation of the probe tip 104 relative to the remainder of the probe 100. For example, in one embodiment, a plurality of articulation cables 110 may be coupled between the probe tip 104 and one or more articulation motors 112. In such an embodiment, by adjusting the tension of the cables 110 via the motor(s) 112, the probe tip 104 may be reoriented within the gas turbine engine 10.

It should also be appreciated that, in several embodiments, the articulation assembly 108 may be configured to be electronically controlled. Specifically, as shown in FIG. 4, the computer 202 may be communicatively coupled to the articulation assembly 108 to allow the computer 202 to adjust the orientation of the probe tip 104 via control of the articulation assembly 108. For instance, in the illustrated embodiment, the computer 202 may be configured to transmit suitable control signals to the articulation motor(s) 112 in order to adjust the tension within the associated cable(s) 110, thereby allowing the computer 202 to automatically adjust the orientation of the probe tip 104 within the gas turbine engine 10.

It should be appreciated that, in other embodiments, the probe 100 may correspond to any other suitable probe configured to be inserted within the gas turbine engine 10 via one of its access ports 62. For instance, in an alternative embodiment, the probe 100 may correspond to a repair probe configured to be inserted within the gas turbine engine 10 to allow a repair procedure to be performed on one or more of the internal engine components, such as a probe used to repair cracks and/or other damage within the engine.

Figure 6:
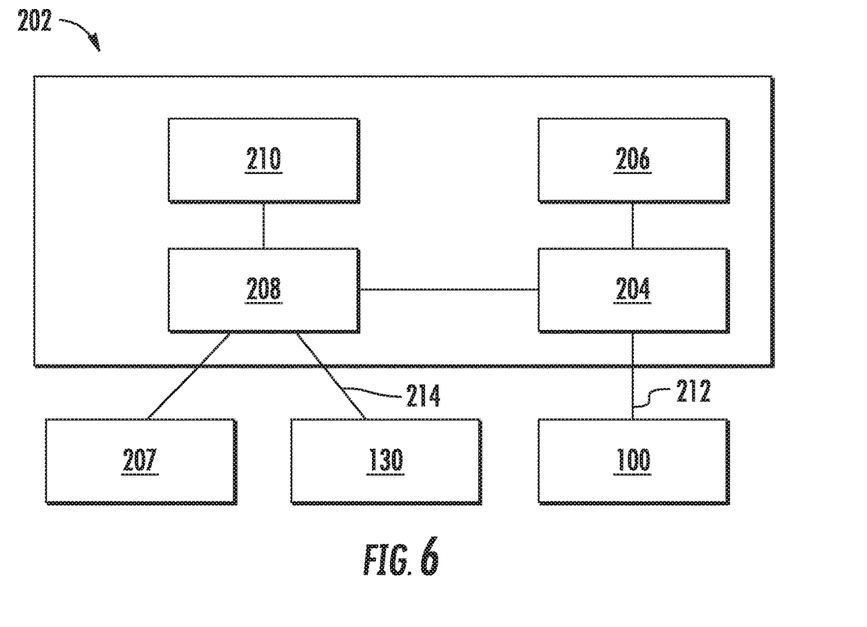
FIG. 6 illustrates one embodiment of a computer configured to automatically insert and orient a probe within a gas turbine engine in accordance with aspects of the present subject matter.
Figure 7:
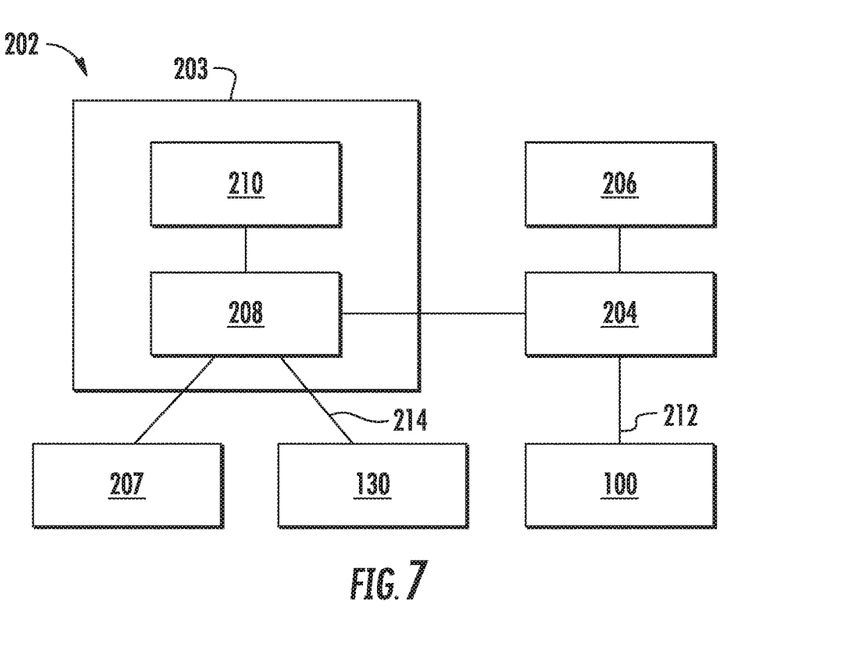
FIG. 7 illustrates another embodiment of a computer configured to automatically insert and orient a probe within a gas turbine engine in accordance with aspects of the present subject matter.

Referring now to FIGS. 6 and 7, block diagrams of a computer 202 according to the present disclosure are illustrated. FIG. 6 shows a computer where a probe computing unit 204 is housed within the same casing as the processor 208 and memory 210. FIG. 7 shows a computer where the probe computing unit is housed in a separate casing from the processor 208 and memory 210. In general, the computer 202 may correspond to any suitable processor-based device and/or any suitable combination of processor-based devices. Thus, in several embodiments, the computing 202 may include one or more processor(s) 208 and associated memory device(s) 210 configured to perform a variety of computer-implemented functions (e.g., performing the methods, steps, calculations and the like disclosed herein). As used herein, the term "processor" refers not only to integrated circuits referred to in the art as being included in a computer, but also refers to a controller, a microcontroller, a microcomputer, a programmable logic controller (PLC), an application specific integrated circuit, and/or other programmable circuits.

Additionally, the memory device(s) 210 may generally comprise memory element(s) including, but not limited to, computer readable medium (e.g., random access memory (RAM)), computer readable non-volatile medium (e.g., a flash memory), a floppy disk, a compact disc-read only memory (CD-ROM), a magneto-optical disk (MOD), a digital versatile disc (DVD) and/or other suitable memory elements. Such memory device(s) 210 may generally be configured to store suitable computer-readable instructions that, when implemented by the processor(s) 208, configure the computer 202 to perform various functions including, but not limited to, determining the current location of the probe tip 104 within the gas turbine engine 10 based at least in part on the signals received from the sensors 120, send signals to the cable insertion unit 130 to orient and/or feed the probe 100, and/or send signals to the articulation assembly 108 to adjust the orientation of the probe tip 104.

For example, computer 202 can receive a signal from the probe 100, attempt to comprehend the surrounding environment by performing various processing techniques on data collected by the sensor 120, and generate an appropriate motion plan through such surrounding environment. The computer 202 can control the probe insertion unit 130 and/or the articulation assembly 108 to orient the probe 100 according to the motion plan.

In some embodiments, the memory device 210 may include an algorithm that learns the most efficient method of moving the probe 100 to a target location 144, by storing and processing data from multiple insertions to the same or similar target locations 144, e.g. machine learning. For example, the machine-learned model can be or can otherwise include one or more various machine or statistical learning model(s) such as, for example, neural networks (e.g., deep neural networks), support vector machines, linear discriminant analysis models, partial least squares discriminant analysis models, random tree models, logistic regression models, naïve Bayes models, K-nearest neighbor models, quadratic discriminant analysis models, anomaly detection models, boosted and bagged decision tree models, C4.5 models, k-means models, and/or other multi-layer non-linear models. Neural networks can include recurrent neural networks (e.g., long short-term memory recurrent neural networks), feed-forward neural networks, and/or other forms of neural networks. For instance, supervised training techniques can be performed to train the model (e.g., using past probe insertion data) to determine an orientation and/or insertion action based at least in part on the feature(s) associated with the signal from the probe 100.

Still referring to FIGS. 6 and 7, the computer 202 includes an installed digital model of the engine 10. Further, the computer is configured to receive at least one signal from the probe 100 and produce a location model. The location model includes at least one of a two dimensional or three dimensional model representing the real time location of the probe tip 104 relative to the turbine engine 10. As such, the location model may be a separate model stored in the memory 210 and/or may be imposed onto the digital model of the engine 10. In a further embodiment, the system 200 may include a first display 206 configured to show the video signal from the optical sensor 120. In another embodiment the system 200 may include a second display 207 configured to show the location model representing the probe's 100 real-time location relative to the turbine engine 10.

In an additional embodiment, the computer 202 may further include a probe computing unit 204. The probe computing unit 204 is configured to receive the signal from the probe 100 and create a modified signal. The processor 208 with memory 210 is configured to store the digital model of the machine and receive the modified signal from the probe computing unit 204. The processor 208 is further communicatively coupled to and in control of the cable insertion unit 130. In such an embodiment, signals to the articulation assembly 108 to adjust the orientation of the probe tip 104 may originate in the processor 208 and pass through the probe computing unit 204. Still, in one embodiment, as shown in FIG. 6, the probe computing unit may be housed within the computer 202 in a single unit. In other embodiments, the probe computing unit 204 may be housed in a separate casing, as shown in FIG. 7.

In a further embodiment, the computer 202 may be communicatively coupled to at least one control system of the engine 10. More specifically, the control system may be used to manipulate the engine 10 before, after, and/or while orienting and feeding the probe 100 into the engine 10. For example, the computer 202 may configured to control the orientation of the compressor blades 82, the turbine blades 68, variable nozzle vanes 78, and/or variable compressor vanes 80.

Figure 8:
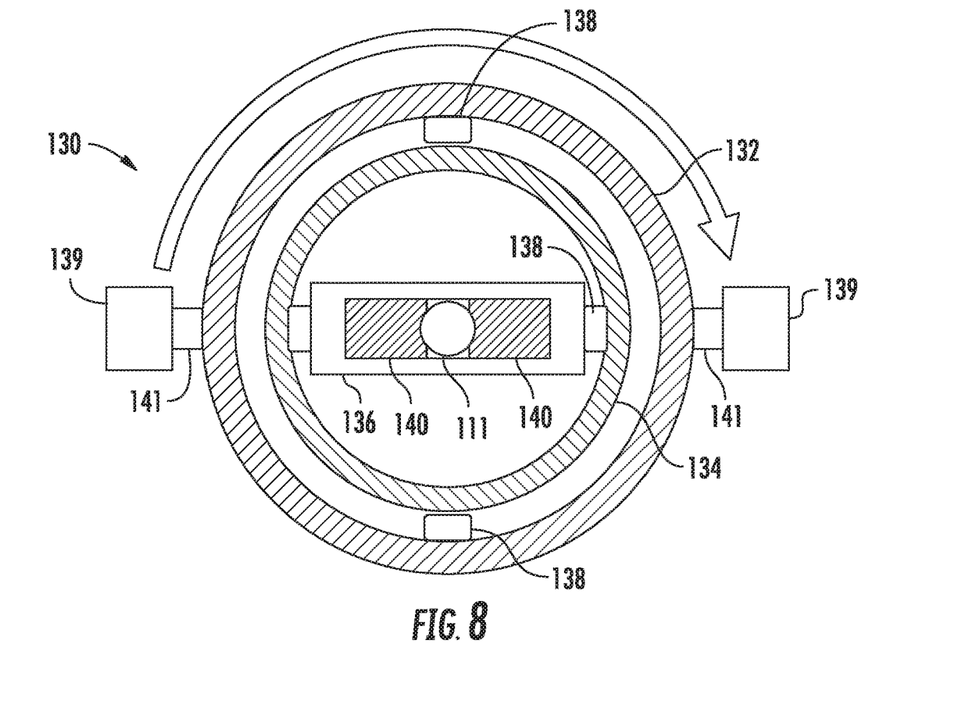
FIG. 8 illustrates one embodiment of a cable insertion unit configured to insert and orient a cable according to aspects of the present subject matter.
Figure 9:
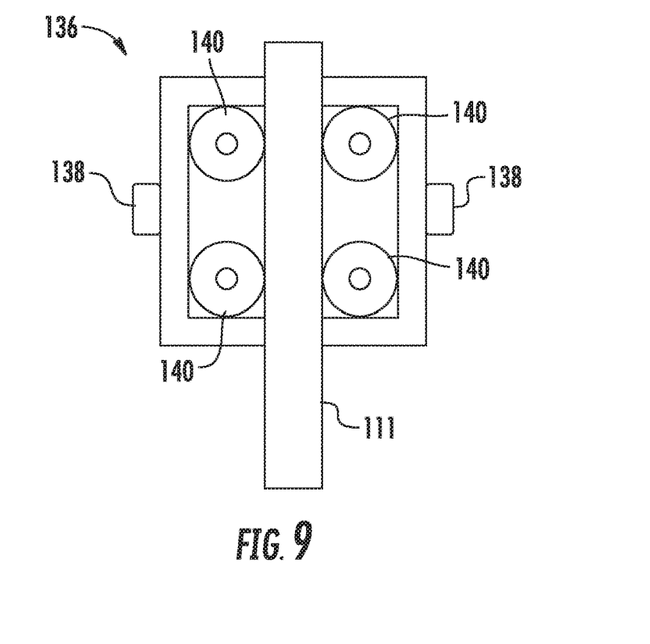
FIG. 9 illustrates one embodiment of the feeding unit of FIG. 8 configured to insert and withdraw a cable according to aspects of the present subject matter.

Referring now to FIGS. 8 and 9, an embodiment of the cable insertion unit 130 according to the present disclosure are illustrated. More specifically, FIG. 6 shows an embodiment where the probe insertion unit 130 may include a 3D gimbal with servo motor control on each of three axes (e.g. pitch, roll, and/or yaw). While FIG. 7 particularly shows a cable feeder 136 component of a 3D gimbal. As such, the cable insertion unit 130 orients and feeds the probe 110 into the machine under the guidance of the computer 202.

Referring particularly to FIG. 8, the 3D gimbal is illustrated with two disks 132, 134 and a feeding unit 136 all of which are coupled together using a plurality of servo motors 138. More specifically, the outermost disk 132 is coupled to servo motors 139 and/or rollers 141 configured to allow the outermost disk 132 to change the roll orientation of the cable 111. The innermost disk 134 is coupled to servo motors 138 configured to change the yaw orientation of the cable 111. Further, the cable feeder 136 is coupled to servo motors 138 configured to change the pitch orientation of the cable 111. As such, the 3D gimbal may receive a signal(s) from the computer 202 to change the orientation of the cable 111 along at least one axis, such as the roll, yaw, and/or pitch. Further, a change in the orientation of the cable 111 may correspond to a change in the orientation of the probe tip 104.

Referring particularly to FIG. 9, the cable feeder 136 is illustrated including a plurality of rubber pinch rollers 140. More specifically, the rubber pinch rollers are in physical contact with the cable 111. As such, friction between the rubber pinch rollers 140 and the cable 111 is used to feed and/or retract the probe 100. For example, the cable feeder 136 may receive a signal from the computer 202 to feed the probe 100 into the engine 10. Conversely, the cable feeder 136 may also receive a signal to retract the probe 100 from the engine 10.

Figure 10:
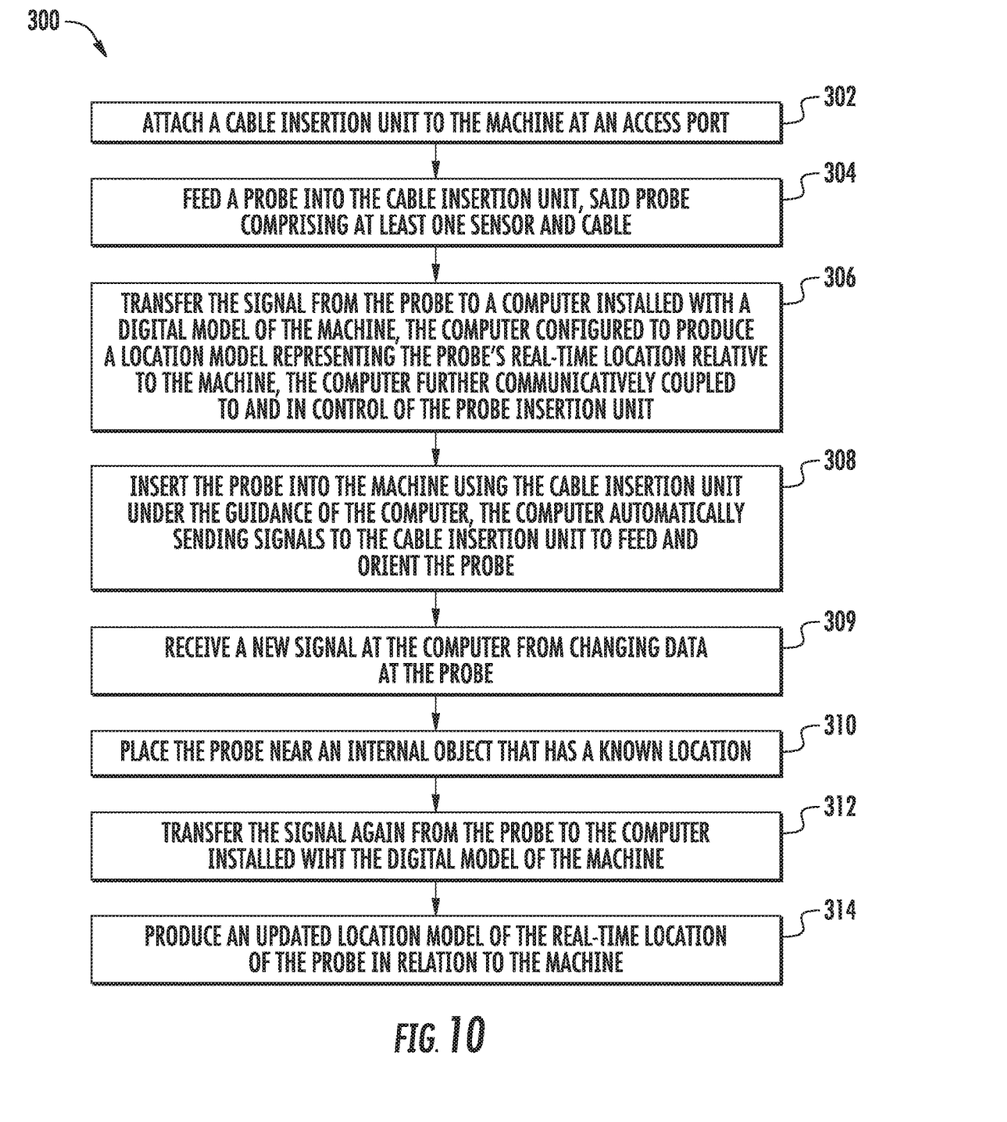
FIG. 10 illustrates a flow diagram of a method for automated probe insertion and orientation into a gas turbine engine according to aspects of the present subject matter.

Referring now to FIG. 10, a flow diagram of one embodiment of a method 300 for automated probe insertion and orientation into a gas turbine engine 10 is illustrated in accordance with aspects of the present subject matter. As shown at 302, the method 300 includes attaching a cable insertion unit 130 to the engine 10 at an access port 62. Another step 304 includes feeding a probe 100 into the cable insertion unit 130. The probe 100 includes at least one sensor 120 and cable 111. As shown at 306, the method 300 includes transferring the signal from the probe 100 to a computer 202 installed with a digital model of the engine 10.

The computer 202 is configured to produce a location model representing the probe's 100 real-time location relative to the engine 10. Further, the computer 202 is communicatively coupled to and in control of the probe insertion unit 130. In some embodiments, the method 300 includes setting an initial location of the probe 100 in the location model to the access port 62 of the engine 10.

As shown at 308, the method 300 also includes inserting the probe 100 into the machine using the cable insertion unit 130 under the guidance of the computer 202. More specifically, the computer 202 automatically sends signals to the cable insertion unit 130 to feed and orient the probe 100 to reach a target location 144, as shown in FIG. 5. In some embodiments, the guidance of the computer 202 may include an algorithm that learns the most efficient method of moving the probe 100 to a target location 144, by storing and processing data from multiple insertions to the same or similar target locations 144.

As shown generally in FIGS. 8 and 9, the cable insertion unit 130 may change the roll, yaw, and/or pitch of the cable 111 and subsequently the orientation of the probe 100. Furthermore, the cable feeder 136 may insert and/or withdraw the probe 100 from the engine 10 under guidance of the computer 202. In a different embodiment, the method 300 may include sending a signal from the computer 202 to the probe 100 to generally adjust an orientation of a probe tip 104. As illustrated in FIG. 4, the probe 100 may include an articulation assembly 108 that allows the orientation of the probe tip 104 to be adjusted within the interior of the engine 10. In some circumstances, the probe 100 and/or cable insertion unit 130 may send a signal to the computer 202 upon sensing resistance in the cable 111. After sensing such resistance, the computer may direct the cable insertion unit 130 to withdraw and/or change the orientation of the cable 111. Similarly, the computer 202 may also send a signal to the probe 100 to change the orientation of the probe tip 104 via the articulation assembly 108.

In some embodiments, the method 300 may include at 309 receiving a new signal at the computer 202 from changing data at the probe 100. As such, a further step 310 includes placing the probe 100 near an internal object that has a known location 142. For example, FIG. 5 illustrates a probe 100 placed within an observable distance of a known location 142. As shown at 312, the method 300 includes transferring the signal again from the probe 100 to the computer 202 installed with the digital model of the engine 10. As shown at 314, the method 300 includes producing an updated location model of the real-time location of the probe 100 in relation to the engine 10. More specifically, the memory 210 of the computer 202 is installed with a digital model of the engine 10. The computer 202 may recognize the known location 142 within the computer model of the engine 10. As such, the computer may update the current real-time location of the probe 100 in the location model to the corresponding coordinates of the known location 142. In some embodiments, the method 300 may include displaying the location model and real-time location of the probe 100 on a display 207.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A system for inserting and orienting a probe into a machine, the system comprising:
a probe, comprising at least one sensor and a cable, the at least one sensor producing at least one signal;
a cable insertion unit configured to orient and feed the probe; and
a computer communicatively coupled to both the probe and the cable insertion unit, the computer comprising an installed digital model of the machine, the computer configured to receive the at least one signal from the probe and produce a location model, the location model comprising at least one of a two dimensional or three dimensional model representing the probe's real-time location relative to the machine,
wherein the cable insertion unit, under the guidance of the computer, orients and feeds the probe into the machine.

2. The system of claim 1, wherein at least one sensor comprises an optical sensor.

3. The system of claim 2, further comprising a first display configured to show the video signal from the optical sensor.

4. The system of claim 1, wherein at least one sensor comprises a proximity sensor.

5. The system of claim 1, wherein the computer further comprises a probe computing unit and a processor with memory, the probe computing unit configured to receive the signal from the probe and create a modified signal, the processor with memory configured to store the digital model of the machine and receive the modified signal from the probe computing unit, the processor further communicatively coupled to and in control of the cable insertion unit.

6. The system of claim 1, wherein the cable insertion unit comprises a 3D gimbal with servo motor control on each of three axes.

7. The system of claim 3, further comprising a second display configured to show the location model representing the probe's real-time location relative to the machine.

8. The system of claim 1, wherein the probe further comprises at least one other sensor, the signal from the sensor(s) transmitted to the computer and used by the computer to determine the real-time location of the probe.

9. The system of claim 1, wherein the computer is communicatively coupled to at least one control system of the machine, the control system used to manipulate the machine before, after, or while orienting and feeding the probe into the machine.

10. A method of automated probe insertion into a machine, the method comprising:
attaching a cable insertion unit to the machine at an access port;
feeding a probe into the cable insertion unit, the probe comprising at least one sensor and a cable;
transferring a signal from the probe to a computer installed with a digital model of the machine, the computer configured to produce a location model representing the probe's real-time location relative to the machine, the computer further communicatively coupled to and in control of the cable insertion unit; and
inserting the probe into the machine using the cable insertion unit under the guidance of the computer, the computer automatically sending signals to the cable insertion unit to feed and orient the probe.

11. The method of claim 10, further comprising receiving a new signal at the computer from changing data at the probe.

12. The method of claim 11, further comprising changing the real-time location of the probe in the location model based on the new signal.

13. The method of claim 12, wherein changing the real-time location of the probe comprises recognizing a known location in the signal and altering the real-time location of the probe to that location in the location model.

14. The method of claim 11, further comprising altering the insertion speed and orientation automatically via the computer to lead the probe to a desired target location.

15. The method of claim 10, further comprising setting an initial location of the probe in the location model to the access port of the machine.

16. The method of claim 10, further comprising sending a signal from the computer to the probe to generally adjust an orientation of a probe tip.

17. The method of claim 10, wherein the guidance of the computer comprises an algorithm that learns the most efficient method of moving the probe to a target location, by storing and processing data from multiple insertions to the same or similar target locations.

18. A method for determining the real-time location of a probe in a machine, the method comprising:
placing the probe near an internal object that has a known location, the probe comprising a sensor and cable;
transferring a signal from the probe to a computer installed with a digital model of the machine; and
producing a location model of the real-time location of the probe in relation to the machine.

19. The method of claim 18, wherein the probe further comprises at least one other sensor, a signal from the other sensor transferred to the computer to determine the real-time location of the probe in the location model.

20. The method of claim 19, further comprising displaying the location model on a display.

* * * * *